US00PP26766P3

(12) United States Plant Patent
Maillard et al.

(10) Patent No.: US PP26,766 P3
(45) Date of Patent: May 31, 2016

(54) APPLE TREE NAMED 'REGALSTAR'

(50) Latin Name: ***Malus domestica* Borkh.**
Varietal Denomination: REGALSTAR

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 127 days.

(21) Appl. No.: 13/999,809

(22) Filed: Mar. 24, 2014

(65) Prior Publication Data

US 2015/0271965 P1 Sep. 24, 2015

(51) Int. Cl.
*A01H 5/08* (2006.01)

(52) U.S. Cl.
USPC ..... Plt./161

(58) Field of Classification Search
USPC ..... Plt./161, 168
See application file for complete search history.

(56) References Cited

PUBLICATIONS

Confidential delivery bill from ASF to Castang dated Mar. 5, 2013; with English machine translation (2 pages).
Delivery bill from Castang to Catafruit dated Mar. 10, 2014; with English machine translation (2 pages).
Redacted invoice from ASF to San Domenec (Catafruit) dated Aug. 8, 2014; with English machine translation (3 pages).
Redacted contract between ASF and Champs des Alpes (Catafruit) dated Jun. 30, 2014; with English machine translation (13 pages).
France plant application for Regaltop (Regalstar) dated Nov. 27, 2012; with English machine translation (2 pages).
European Community plant application for Regaltop (Regalstar) No. 2012/2710 dated Nov. 27, 2012; with English machine translation (2 pages).
Morocco plant application for Regalstar No. 611/15 dated Oct. 22, 2015; with English machine translation (36 pages).
France Office refusal of denomination Regaltop dated Jan. 14, 2013; with English machine translation (2 pages).
European Community Office refusal of denomination Regaltop dated Dec. 17, 2012; with English machine translation (4 pages).
European Community denomination proposal for Regalqueen dated Jan. 2, 2013; with English machine translation (3 pages).
European Community Office refusal of denomination Regalqueen dated Jan. 14, 2013; with English machine translation (6 pages).
European Community denomination proposal for Regalstar dated Jan. 25, 2013; with English machine translation (2 pages).
European Community Official Gazette excerpt for Regalstar dated Apr. 15, 2013; in English (10 pages).
Information sheet for Regalstar dated Jul. 24, 2013; with English machine translation (4 pages).
Commercial brochure for Regalstar dated 2015; with English machine translation (4 pages).

*Primary Examiner* — June Hwu
(74) *Attorney, Agent, or Firm* — Westerman, Hattori, Daniels & Adrian, LLP

(57) ABSTRACT

A new and distinct variety of apple tree denominated 'REGALSTAR' produces high yield of fruits with large size and round slightly flattened shape, a red skin color, very firm, and with exceptional eating quality; the fruit is further characterized by its good handling and storage qualities.

3 Drawing Sheets

Latin name of the genus and species of the plant claimed: *Malus domestica* Borkh.

Variety denomination: 'REGALSTAR'.

BACKGROUND OF THE NEW VARIETY

Field of the Invention

In the field of plant genetics, we conduct an extensive and continuing plant-breeding program including the organization and reproduction of orchard trees, among which apple, peaches, nectarines, apricots, and cherries are exemplary. It was against this background of our activities that the present variety of apple tree was originated and reproduced by us in our experimental orchard located near Elne, Pyrénées Orientales, France.

ORIGIN OF THE VARIETY

The present invention relates to a new a distinct variety of apple tree *Malus domestica* Borkh. which has been given the variety denomination 'REGALSTAR'. This tree produces fruits with a long shelf life without alteration after harvesting, very good eating quality with a yellow flesh for fresh market in October in the Pyrénées Orientales department, France. Contrast is made to 'FUJI' apple tree (non patented) for reliable description. 'REGALSTAR' is a promising candidate for commercial success in that it produces very attractive fruits having a long shelf life.

The present new variety of apple tree (*Malus domestica* Borkh.) was developed by us in our experimental orchard located in France. 'REGALSTAR' apple tree originated in a cultivated area of the South of France, in the Pyrénées-Orientales department where it was also tested. This zone also called Roussillon is subject to a Mediterranean climate. The winter is generally sweet and the summer is hot and dry. The total amount of cold hours lower than 7° C. (Celsius) varies from 600 hours to 1200 hours. The total amount of sunshine hours is an average of 2400 hours to 2800 hours per year. The prevailing wind is called "Tramontane": it dries the air and clear the sky from cloud but its intensity can be strong and affect the harvest, fruits quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen and the summer is dry with a few thunderstorms.

The 'REGALSTAR' variety results from a pollinated cross between a variety named 'ARIANE 6407 RT' (non patented) which was used as a seed parent and a variety named 'ROSE BOW' (non patented), which is a clone of 'Cripps Pink' (U.S. Plant Pat. No. 7,880) PINK LADY® and was used as the pollen parent.

'REGALSTAR' variety was provisionally designated, tested under number 03.3E194.08.

The 'REGALSTAR' variety was obtained by hybridizing and propagated by grafting on a 'M9EMLA' (non-patented) rootstock trees. It has been determined to have unique tree and fruits characteristics making it worthy for commercial fresh fruits production. There are no known effects of the standard rootstock tree set forth above on the scion cultivar. Asexually propagated plants remained true to the original tree and all characteristics of the tree and the fruit were transmitted. The plant was asexually reproduced by us in Les Régalines, Route d'Alenya, La Prade de Mousseillous, 66200 ELNE, Pyrénées Orientales, France. More particularly, the plant was reproduced by grafting.

SUMMARY OF THE NEW VARIETY

The new variety 'REGALSTAR' produces fruits of large size, very firm and juicy, and with a luminous red color. The blooming period is medium for the variety, namely in the beginning of April or mid-April. The maturity period is late or very late, generally during the first decade of October in the South of France. However, it was observed that its early date of blooming and maturity seems to be highly dependant on climatic conditions.

BRIEF DESCRIPTION OF THE DRAWINGS

The accompanying photographs show typical specimens of the new variety as depicted in color as nearly true as is reasonably possible in color illustrations of this character. These specimens were obtained at the Elne Experiment Station, South of France.

Figure 1:
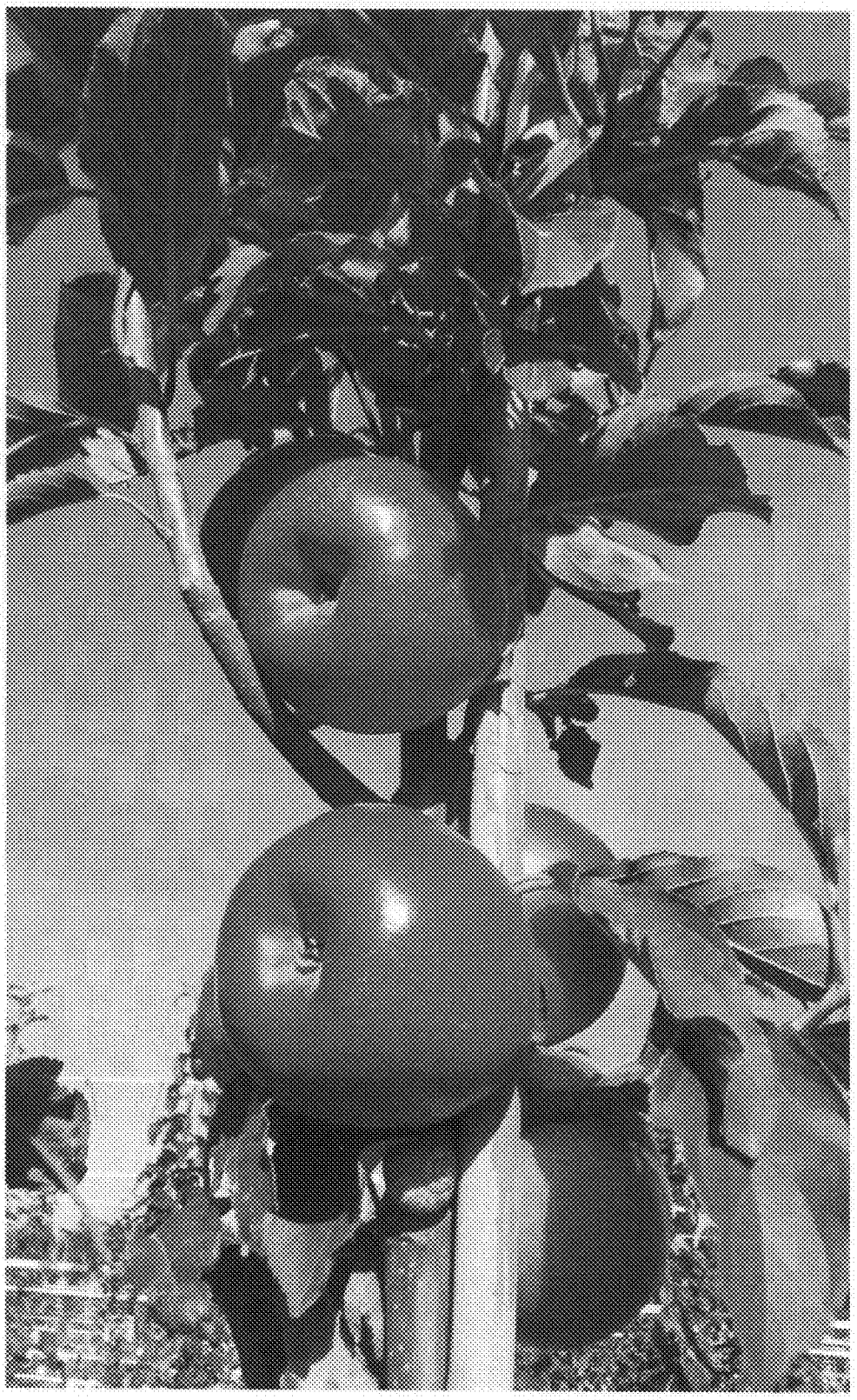
FIG. 1 is a color photograph which shows a branch of a tree of the new variety in orchard, bearing fruits.
Figure 2:
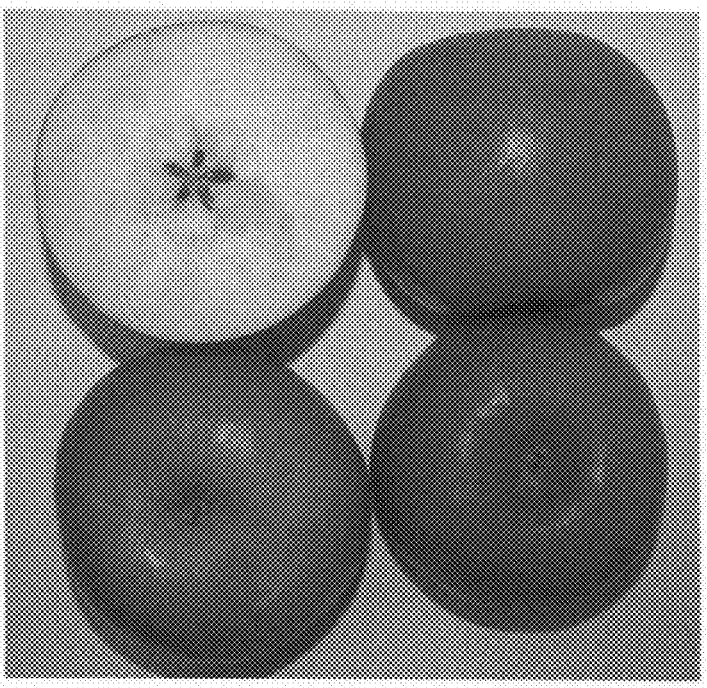
FIG. 2 is a color photograph which shows three whole fruits of the new variety, and a fourth fruit, cut in a half in transverse cross section for depicting the fruit flesh, the seeds and the locules of the new variety.
Figure 3:
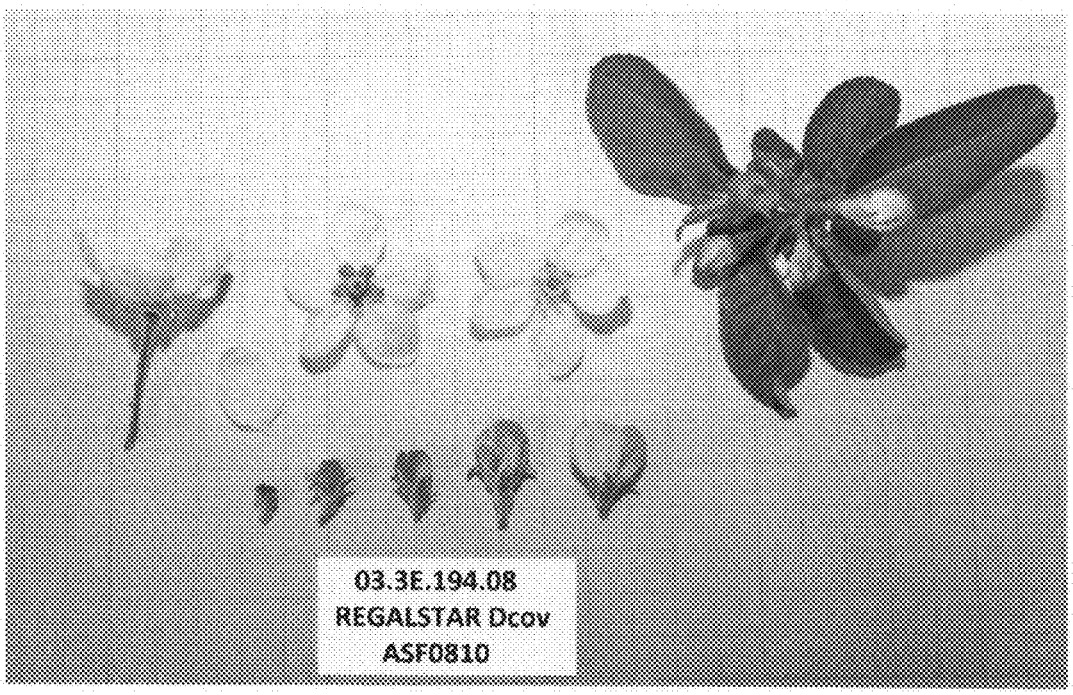
FIG. 3 shows typical flowers of 'REGALSTAR' variety at blooming with some leaves for depicting the flower buds at different stages of development, the reverse and side view of the flowers and the reproductive organs of the new variety.
Figure 4:
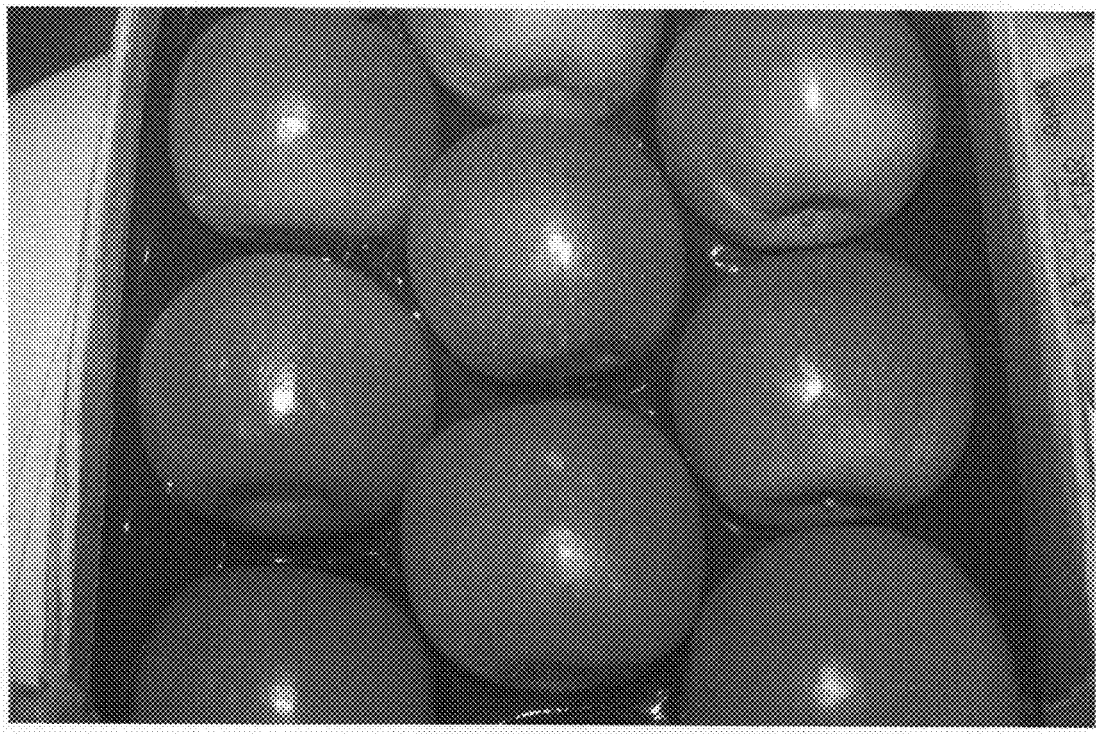
FIG. 4 is a color photograph that shows a close view of typical fruits of the new variety 'REGALSTAR' at ripening time.

Due to chemical development, processing and printing, the leaves and fruits depicted in these photographs may or may not be accurate when compared to the actual botanical specimen.

DETAILED BOTANICAL DESCRIPTION OF THE VARIETY

The following is a detailed botanical description of the new variety of apple tree, its flowers, foliage and fruit, as based on observations of specimens grown near Elne, South of France, with color in accordance with The R.H.S. Color Chart (Fourth Edition) provided by The Royal Horticultural Society of Great Britain.

The trees, flowers and fruits may vary in slight detail due to variations in soil type, cultural practices and climatic conditions.

The main characteristics of this new variety of sweet apple are a large fruit size with a color of skin considered red. The fruit flesh is yellow. The fruit is very firm.

The time of beginning of flowering is medium whereas the time of beginning of fruit ripening is considered late or very late.

In comparison to 'FUJI' apple tree variety (non-patented'), 'REGALSTAR' apple tree blooms approximately at the same time and ripens 4 days later than 'FUJI'. The skin coloration of 'FUJI' variety is considered pink red covering 50 to 70% of skin whereas the skin coloration of 'REGALSTAR' is red on 95 to 100% of the fruit skin. Flavor of 'REGALSTAR' fruits is considered semi-sweet, very sugary and aromatic, with a Brix between 17.0 and 19.0 degrees whereas 'FUJI' fruits show a sweet taste and are less sugary, with a Brix between 13.0 and 15.0 degrees. 'FUJI' fruits have an irregular shape, whereas 'REGALSTAR' variety produces fruits that show a very regular shape and less flattened than 'FUJI' fruits.

Moreover, firmness of 'FUJI' fruits is considered medium whereas 'REGALSTAR' fruits are considered very firm. The texture of 'FUJI' fruits is considered semi-crunchy. On the contrary, the texture of 'REGALSTAR' fruits is very crunchy and melting.

Finally, 'REGALSTAR' variety produces fruits regularly, without alternation, contrary to 'FUJI' variety, which may show an alternation in fruits production.

Compared to its parent 'ARIANE 6407 RT' (non patented) and 'ROSE BOW' (non patented), which have an acidulous flavor, the new variety 'REGALSTAR' presents a semi sweet taste. The fruit texture of the new variety 'REGALSTAR' is crunchy melty whereas the fruit texture of 'ARIANE 6407 RT' is crunchy melty slightly fibrous and the fruit texture of 'ROSE BOW' is crunchy melty but also slightly downy. The fruit skin color of the new variety 'REGASLTAR' is red with almost no roughness. In comparison, the fruit skin color of the 'ARIANE 6407 RT' is considered red with roughness both in the eye basin and in the stalk cavity. The fruit skin color of the male parent 'ROSE BOW' is two-colored with pink and light yellow.

The new variety of apple tree 'REGALSTAR' is very few sensitive to apple scab (*Venturia inaequalis*) whereas its female parent 'ARIANE 6407 RT' is considered resistant to apple scab and its male parent 'ROSE BOW' is considered sensitive.

The tree of 'REGALSTAR' variety is much ramified, just as 'ROSE BOW tree, whereas the ramification of the tree of 'ARIANE 6407 RT' is considered medium to low. The bearing of 'REGALSTAR' and ROSE BOW' varieties is considered rapid and important every year. In comparison, the female parent 'ARIANE 6407 RT' has a slow and medium bearing.

The following varieties are considered as good pollinators for the new variety 'REGALSTAR': 'Cripps Pink' (U.S. Plant Pat. No. 7,880) PINK LADY®, 'ARIANE', 'FUJI' and 'Early Red One' (U.S. Plant Pat. No. 3,556).

DETAILED DESCRIPTION

Referring more specifically to the pomological details of this new and distinct variety of apple tree, the following has been observed on trees on their sixth growing season (five year of production) under the ecological conditions prevailing at the orchards located near the town of Elne, Pyrénées-Orientales department, France.

All observations have been done on rootstock cultivar. The rootstock was a 'M9EMLA' (non-patented) tree. All major color code designations are by reference to The R.H.S. Color Chart (Fourth Edition) provided by The Royal Horticultural Society of Great Britain.

TREE

Generally: The first year the apple tree is generally cut at 2.50 meters height. The length in one year for each lateral shoot varies from 0.60 meters to 0.80 meters. We are cutting the apple trees during the second year to a height of 2.50 meters. The form of the apple trees is cylindrical and the diameter is limited to 1 meter.

*Size*.—Medium to high as compared to other commercial apple cultivars. The tree size the first year was approximately 2.50 meters. The tree was pruned during each following dormant season to a height of approximately 2.50 meters. Current season's shoots growth could reach 0.80 meters. So the tree size from the second year (second and next years) reached a final height of 3.10 to 3.30 meters with current seasons shoots length comprised.

*Spread*.—Approximately 1.0 meter with a cylindrical shape. The whole orchard was oriented to a central leader organization, with tree lines spaced of 4.0 meters and trees spaced of 1 meter in a same tree line.

*Vigor*.—Strong, tree growth reaching 0.60 to 0.80 meters the first growing season.

*Productivity*.—Very good productivity, every year and without alternation. The new variety produces adequate fruit set annually on a regular basis. The number of the fruit set varies with the prevailing climatic conditions and cultivar practices employed during the bloom period, and is therefore not distinctive of the present variety.

*Bearer*.—Very regular every year.

*Type of bearing*.—On spurs and long shoots.

*Type*.—Ramified.

*Habit*.—Spreading.

*Form*.—Naturally semi-spread.

*Hardiness*.—Hardy in all stone fruit growing areas of France and especially where the chilling requirement is between 350 and 1200 hours. No injury with a temperatures as low as −12° C. in winter. Good resistance to late frosts.

Trunk:

*Size*.—Medium. Approximately 22.0 to 26.0 millimeters ($2^{nd}$ growing season) and 84.0 millimeters ($4^{th}$ growing season) above 20.0 centimeters above the ground.

*Bark texture*.—Smooth with lenticels.

*Lenticels*.—Medium number of lenticels. The number of lenticels reaches 2 to 3 lenticels per $cm^2$.

*Lenticels size*.—Approximately 1.5 millimeters height and between 6.0 and 8.0 millimeters width ($4^{th}$ growing season).

*Lenticels color*.—Color of lenticels is considered grey orange (RHS Greyed Orange 164 B to RHS Greyed Orange 164 C).

*Bark color*.—Grey brown (RHS Grey Brown N199 A).

Branches:

*Diameter*.—Branches at the 2nd growing season have an average diameter of 9.0 to 12.0 millimeters.

*Length*.—Between 68.0 and 80.0 centimeters.

*Surface texture*.—Wood which is several years old has no furrowed appearance.

*Lenticels*.—Lenticels on branches at the 2nd growing season are small with a diameter of about 1.0 millimeter and a round shape.

*Color*.—Branches are brown (RHS Grey Brown 199 A or RHS Grey Brown N199 A).

*Crotch angles*.—Between 80 degrees and 90 degrees from the supporting branch. This particular characteristic is not considered distinctive of the variety, however.

*Internode*.—Generally from 25.0 to 28.0 millimeters length.

Current season shoots:

*Diameter*.—Average diameter from 4.0 to 6.0 millimeters.

*Length*.—Between 30.0 and 40.0 centimeters.

*Surface texture*.—Smooth to rough, due to lenticels.

*Lenticels*.—Considered small with a diameter of about 1.0 millimeter and a round shape.

*Crotch angles*.—Between 40 degrees and 45 degrees from the supporting branch. This particular characteristic is not considered distinctive of the variety, however.

*Internode*.—Generally from 22.0 millimeters to 26.0 millimeters length.

*Color*.—The color of current season shoots is considered grey brown (RHS Brown N199 B) on lower part of shoots, whereas the upper part is darker and colored in brown (RHS Brown 200 A to RHS Brown 200 B).

Bud scales:

*Size*.—Medium to large.

*Shape*.—Elongated and conic in shape.

*Surface texture*.—Pubescent.

*Color*.—The inside of the bud scales is yellow green (RHS Yellow Green 145 A) and the outside of the bud scales is purple brown (RHS Greyed Purple 183 A).

LEAVES

*Size*.—Medium for the species. The ratio leaf length/leaf width is 1.77.

*Length*.—Between 96.0 and 114.0 millimeters without leaf petiole. The medium length is about 103.3 without leaf petiole.

*Width*.—Between 49.0 and 69.0 millimeters without leaf petiole. The medium width is about 58.3 millimeters without leaf petiole.

*Leaf form in transverse section*.—Concave.

*Leaf form*.—Ovoid and round.

*Apex*.—Short, pointed and acuminate.

*Base*.—Round-shaped.

*Margins*.—Slightly undulating.

*Margins shape*.—Crenate.

*Surface texture*.—Low pubescence on lower surface of the leaves. No pubescence on upper surface.

Leaf color:

*Upper leaf surface*.—Green (RHS Yellow Green 147 A).

*Lower surface*.—Considered yellow green (RHS Yellow Green 146 A to RHS Yellow Green 146 B or RHS Yellow Green 147 B), slightly lighter than upper leaf surface color.

Leaf veins:

*Leaf venation*.—Pinnately veined.

*Color*.—The color of the veins is considered yellow green (RHS Yellow Green 145 C).

Leaf petioles:

*Size*.—Medium to large.

*Length*.—About 23.0 to 30.0 millimeters.

*Diameter*.—About 2.0 to 2.5 millimeters.

*Color*.—Upper surface light green (RHS Yellow Green 144 A to RHS Yellow Green 144 B). Lower surface light green (RHS Yellow Green 146 C) with a brown purple pigmentation (RHS Greyed Purple 187 B to RHS Greyed Purple 187 C).

*Grooves on petiole*.—Not prominent. Slightly marked.

Leaf stipules:

*Generally*.—Two stipules are observed.

*Size*.—Considered small.

*Length*.—Approximately 12.0 millimeters.

*Shape*.—Elliptic and elongated.

*Color*.—Leaf stipules show the same color as whole leave color. Upper stipules surface is considered green (RHS Yellow Green 147 A) and lower stipules surface is yellow green (RHS Yellow Green 146 A to RHS Yellow Green 146 B or RHS Yellow Green 147 B).

FLOWERS

Flower buds:

*Generally*.—At pre-floral stage of development, the floral bunches are make up with 5 to 6 floral buds having a conic shape with a round tip. Their form is evolving until blooming, with variables dimensions. Just before blooming, floral buds are approximately 10.0 millimeters in diameter and approximately 17.0 millimeters long.

*Color*.—This characteristic is dependent upon the proximity to bloom. At pre-floral stage of development, the bottom of the flowers buds, or calyx formed by sepals, is of green color (RHS Greyed Green 194 B to RHS Greyed Green 194 C). The corolla formed by petals, is generally violet (RHS Red 58 A or RHS Red 64 A to RHS Red 64 B).

*Hardiness*.—The buds are considered hardy under typical central Pyrénées-Orientales department climatic conditions. No winter injury was noted during the last several years of evaluation in the central Pyrénées-Orientales department, with winter temperatures as low as −10° C. in January. The current variety has not been intentionally subjected to drought or heat stress, but the variety showed a very good resistance in orchard to temperatures up to 42° C. with an average temperature between 28° C. and 30° C. during 3 weeks in summer.

*Date of bloom*.—Generally early in April. The first bloom was observed on Apr. 13 until Apr. 22, 2010.

*Blooming time*.—Considered medium in relative comparison to other commercial apple cultivars grown in the Pyrénées-Orientales department, France. The date of bloom varies slightly with climatic conditions and cultural practices. Thus, the full bloom was observed from Apr. 13 to Apr. 22, 2010, then from Apr. 3 to Apr. 12, 2011, then from Apr. 9 to Apr. 22, 2012 and from Apr. 17 until Apr. 28, 2013.

*Blooming period*.—Average 10 to 13 days. This characteristic varies slightly with the prevailing climatic conditions.

*Flower type*.—The variety is considered to have a showy type flower.

*Flower size*.—Considered medium. Average diameter of the corolla is between 22.0 and 28.0 millimeters when totally opened.

*Flower bud frequency*.—Generally 5 to 6 flower buds appear per node.

Petal:

*Size*.—Considered medium for the species.

*Length*.—Generally about 12.3 millimeters.

*Width*.—Generally about 8.2 millimeters.

*Petal form*.—Round, elongated, with slightly curved margins.

*Petal base*.—Round.

*Petal margins*.—Slightly curved and soft.

*Petal count*.—Nearly always 5.

*Arrangement of petals*.—Generally free.

*Petal texture*.—Smooth, soft and glabrous.

*Petal color*.—White (RHS White 155 D).

*Fragrance*.—Soft.

Petal apex:

*Generally*.—The petal apices are generally round shaped.

Flower pedicel:

*Length*.—Average length between 15.0 to 21.0 millimeters.

*Diameter*.—Average 1.9 millimeters.

*Color*.—Light green (RHS Yellow Green 146 C to RHS Yellow Green 146 D).

Calyx:

*Color*.—The calyx is green (RHS Green 138 A).

*Texture*.—The inner surface is smooth.

Sepals:

*Size*.—Usually considered medium.

*Length*.—Approximately 8.7 millimeters.

*Width*.—Approximately 2.9 millimeters.

*Number*.—Generally 5 sepals per flower.

*Sepal form*.—Triangular.

*Texture*.—Pubescent.

*Color*.—Outer surface of the sepals is green (RHS Greyed Green 194 A to B).

Stamens:

*Average number of stamens per flower*.—Approximately 20 to 22 stamens per flower.

Pollen:

*Generally*.—Present.

*Color*.—Pollen has a yellow color (approximately RHS Yellow 1 C) which may evolve with maturity.

Filaments:

*Size*.—Variable in length, approximately between 5.0 and 7.0 millimeters in length, generally higher than pistil's length.

*Color*.—Considered as white (RHS White 155 C).

Pistil:
*Generally.*—1 pistil is present.
*Length.*—Approximately from 13 millimeters long including the ovary, generally smaller than filament's length.
*Color.*—Considered pale green (RHS Yellow Green 149 B to RHS Yellow Green 149 C).

Stigma:
*Diameter.*—Approximately 0.9 millimeter.
*Shape.*—Elliptic.
*Color.*—Light green (RHS Yellow Green 151 A).

Ovary:
*Length.*—Approximately 3.0 millimeters.
*Diameter.*—Approximately 2.0 millimeters.
*Texture.*—Pubescent.
*Color.*—Grey green (RHS Greyed Green 145 C).

Anthers:
*Diameter.*—Approximately 1.5 millimeters.
*Size.*—Medium.
*Form.*—Oblong.
*Color.*—Considered Yellow (RHS Yellow 5 D).

FRUITS

*Maturity when described.*—Very firm at maturity.
*Date of first picking.*—Oct. 10, 2009, varies slightly with climatic conditions.
*Date of last picking.*—Oct. 10, 2013 varies slightly with climatic conditions. The harvest is generally performed in two runs.
*Ripening period.*—Generally during the first two weeks of October. Last known picking times carry on Oct. 10 to Oct. 15, 2009, then from Oct. 15 to Oct. 20, 2010, then from Oct. 5 to Oct. 15, 2011, then from Sep. 27 to Oct. 4, 2012, and then from Oct. 10 to Oct. 17, 2013.

Size:
*Generally.*—Considered large, with a homogeneous size between them.
*Average transversal diameter.*—About 70.0 to 76.0 millimeters.
*Average axial diameter.*—About 60.0 to 65.0 millimeters.
*Typical weight.*—Generally between 170.0 to 205 grams. This characteristic is highly dependent upon the prevailing cultural practices, and therefore is not particularly distinctive of the variety.
*Position of the maximum diameter.*—At the middle of the fruit.

Fruit form:
*Generally.*—Round and slightly flattened.
*Fruit ribbing.*—Absent.
*Fruit suture.*—Absent.
*Form of the ventral surface.*—Smooth.
*Apex.*—Generally slightly depressed, non prominent.
*Base.*—Wide-mouthed, shallow.

Fruit stem:
*Length.*—Between 12.0 and 14.0 millimeters.
*Diameter.*—About 3.0 millimeters.
*Color.*—Light green (RHS Yellow Green N144 A).

Stem cavity:
*Form.*—Acuminate and narrow.
*Depth.*—Average depth between 10.0 and 13.0 millimeters.
*Width.*—Between 14.0 and 17.0 millimeters.

Fruit eye basin:
*Form.*—Wide-mouthed, shallow and smooth.
*Depth.*—Average depth between 13.0 and 17.0 millimeters.
*Width.*—Between 23.0 and 27.0 millimeters.

Calyx:
*Generally.*—Round-shaped.
*Size.*—Approximately 7.0 millimeters.
*Form.*—Open.
*Calyx lobes.*—Generally, these lobes are not prominent on the fruit.
*Calyx tubes.*—Conical and narrow, with the floral stamens in the tubes.
*Length of sepals.*—Between 5.0 and 6.0 millimeters.
*Position.*—In the middle.

Fruit skin:
*Thickness.*—Considered very thick and the adherence of skin to flesh strong to medium, depending on the fruit maturity.
*Texture.*—Glabrous.
*Tendency to crack.*—None.
*Taste.*—Semi-sweet.
*Bloom of skin.*—Absent.
*Greasiness of skin.*—Absent.

Lenticels:
*Number.*—About 3 lenticels per $cm^2$ of fruit skin.
*Size.*—Small.
*Form.*—Round.
*Diameter.*—Approximately 1.0 to 1.8 millimeters.
*Color.*—Yellow brown (RHS Greyed Yellow 161 C to RHS Greyed Yellow 161).

Skin color:
*Over color.*—This over color is considered red and very luminous (RHS Red 46 A) and covers 80 to 90% of fruit skin.
*Striping.*—Absent.
*Ground color.*—The ground color is orange red (RHS Red 45 A) and covers at the most 10 to 20% of the fruit skin.

Russeting:
*Russet around stem cavity.*—Very low.
*Russet on cheek.*—Absent or very weak.
*Russet around eye basin.*—Absent or very weak.

Flesh:
*Texture.*—Very crunchy, melty.
*Fibers.*—No fibers.
*Firmness.*—Very firm.
*Aroma.*—Present and pronounced.
*Juice.*—Very juicy at ripeness.
*Taste.*—Semi sweet.
*Brix.*—Superior to 17.0 degrees until 19.0 degrees, varies slightly with amount of fruit per tree and climatic conditions.
*Color.*—Yellow (RHS Yellow 11 D) at ripening time.
*Aperture of locules in transverse section.*—Moderately open.

Fruit core:
*Size.*—Small.
*Position.*—At the middle of the fruit.
*Distinctness of core line.*—Distinct.

Seeds:
*Count.*—Generally 10 seeds are present.
*Number of seeds per locule.*—Usually 2 seeds per locule.
*Size.*—Medium to large.
*Length.*—Approximately 9.0 millimeters.

*Width*.—Approximately 5.0 millimeters.
*Form*.—Elliptic and pointed at the top.
*Texture*.—Smooth.
*Color*.—Considered orange Brown (RHS Brown 175 A) at ripeness.
*Kernel*.—Considered white (RHS White 155 D).

Use: Dessert, fresh products, fruit juice.
*Market*.—Local and long distance. On the tree fruits can stay 10 days while keeping good gustative qualities. The lifetime after picking is also good.

Keeping quality: Good, held well for 3 to 4 months in cold storage at 1° C. and maintained good appearance and eating quality. At room temperature (18° C.), fruits are well preserved for about 2 months.

Shipping quality: Good, showed minimal bruising or scarring during picking, packing and shipping trials.

Plant/fruit disease resistance/susceptibility: In our growing conditions, no particular symptom was noticed except for apple scabs (2 small spots observed in 2012).

Robustness to winter: Very good for trees and flower buds.

Tolerance to dryness: Good.

The present new variety of apple tree, its, flowers, foliage and fruit herein described may vary in slight detail due to climate, soil conditions and cultural practices under which the variety may be grown. The present description is that of the variety grown under the ecological conditions prevailing near Elne, Pyrénées Orientales (66), France (FR).

We claim:

1. A new and distinct variety of apple tree, substantially as illustrated and described, characterized by its high yield, its fruit and especially by its large size and round slightly flattened shape, its red skin color, its firmness, and exceptional eating quality; the fruit is further characterized by its good handling and storage qualities.

* * * * *